United States Patent
Lee et al.

(10) Patent No.: US 7,696,387 B2
(45) Date of Patent: Apr. 13, 2010

(54) METHOD FOR PREPARING CATALYST FOR PARTIAL OXIDATION OF METHYLBENZENES

(75) Inventors: Won Ho Lee, Daejeon (KR); Dong Il Lee, Gyeonggi-do (KR); Jong Hyun Chae, Daejeon (KR); Hyun Kyung Yoon, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/435,212

(22) Filed: May 17, 2006

(65) Prior Publication Data
US 2006/0281632 A1   Dec. 14, 2006

(30) Foreign Application Priority Data
May 19, 2005   (KR) .................. 10-2005-0041971

(51) Int. Cl.
*B01J 23/00*   (2006.01)
*B01J 21/00*   (2006.01)
*B01J 20/00*   (2006.01)
*C07C 45/00*   (2006.01)
*C07C 45/90*   (2006.01)

(52) U.S. Cl. ................ 568/431; 502/178; 502/305; 502/308; 502/309; 502/349; 502/350; 502/415; 502/439

(58) Field of Classification Search ............... 502/305, 502/308, 309, 178, 349, 350, 439; 568/431
See application file for complete search history.

(56) References Cited

U.S. PATENT DOCUMENTS

| | | | | |
|---|---|---|---|---|
| 3,845,137 A | | 10/1974 | Magder | |
| 4,017,547 A | | 4/1977 | Simmons et al. | |
| 4,269,737 A | * | 5/1981 | Grenoble et al. | 502/204 |
| 4,374,293 A | * | 2/1983 | Burrington et al. | 585/410 |
| 4,504,681 A | * | 3/1985 | Armor | 564/267 |
| 4,522,936 A | * | 6/1985 | Kukes et al. | 502/249 |
| 4,833,113 A | * | 5/1989 | Imanari et al. | 502/309 |
| 4,929,586 A | * | 5/1990 | Hegedus et al. | 502/217 |
| 5,037,792 A | * | 8/1991 | Luck | 502/307 |
| 5,116,801 A | * | 5/1992 | Luck | 502/307 |
| 5,137,855 A | * | 8/1992 | Hegedus et al. | 502/84 |
| 5,229,347 A | * | 7/1993 | Prada et al. | 502/221 |

(Continued)

FOREIGN PATENT DOCUMENTS

JP   47-002086   1/1972

(Continued)

*Primary Examiner*—Cam N Nguyen
(74) *Attorney, Agent, or Firm*—McKenna Long & Aldridge LLP

(57) ABSTRACT

The present invention relates to a novel method for preparing a catalyst for partial oxidation of methylbenzenes, comprising, (a) a step of preparing a solution or slurry of the compounds comprising tungsten; (b) a step of supporting the solution or slurry obtained in the step (a) on inorganic carrier; (c) a step of drying the catalyst obtained in the step (b); and (d) a step of calcining the dried catalyst obtained in the step (c), characterized in that the ratio of the pore volume of inorganic carrier and the volume of the solution or slurry in the step (b) is 1:0.9~1.1, and the catalyst provides superior aromatic aldehydes selectivity to those prepared by the conventional impregnation or heat evaporation method over a wide range of conversion rate.

9 Claims, 1 Drawing Sheet

U.S. PATENT DOCUMENTS

| | | |
|---|---|---|
| 5,324,702 A | 6/1994 | Yoo et al. |
| 5,753,582 A * | 5/1998 | Garcin et al. ............... 502/323 |
| 5,981,426 A * | 11/1999 | Langford et al. ............ 502/309 |
| 6,037,306 A * | 3/2000 | Xia et al. .................... 502/315 |
| 6,120,747 A * | 9/2000 | Sugishima et al. ....... 423/240 S |
| 6,458,737 B1 | 10/2002 | Kishimoto et al. |
| 6,793,875 B1 | 9/2004 | Shaw et al. |
| 6,870,014 B2 * | 3/2005 | Steinbrenner et al. ......... 526/90 |
| 2002/0188159 A1 * | 12/2002 | Kishimoto et al. ........... 568/431 |
| 2003/0186806 A1 * | 10/2003 | Steinbrenner et al. ....... 502/305 |
| 2006/0094906 A1 | 5/2006 | Lee et al. |

FOREIGN PATENT DOCUMENTS

| | | |
|---|---|---|
| JP | 48-097830 | 3/1972 |
| JP | 48-47830 | 7/1973 |
| JP | 2001-198464 | 7/2001 |
| KR | 20040089376 | 5/2006 |

* cited by examiner

DRAWING 1
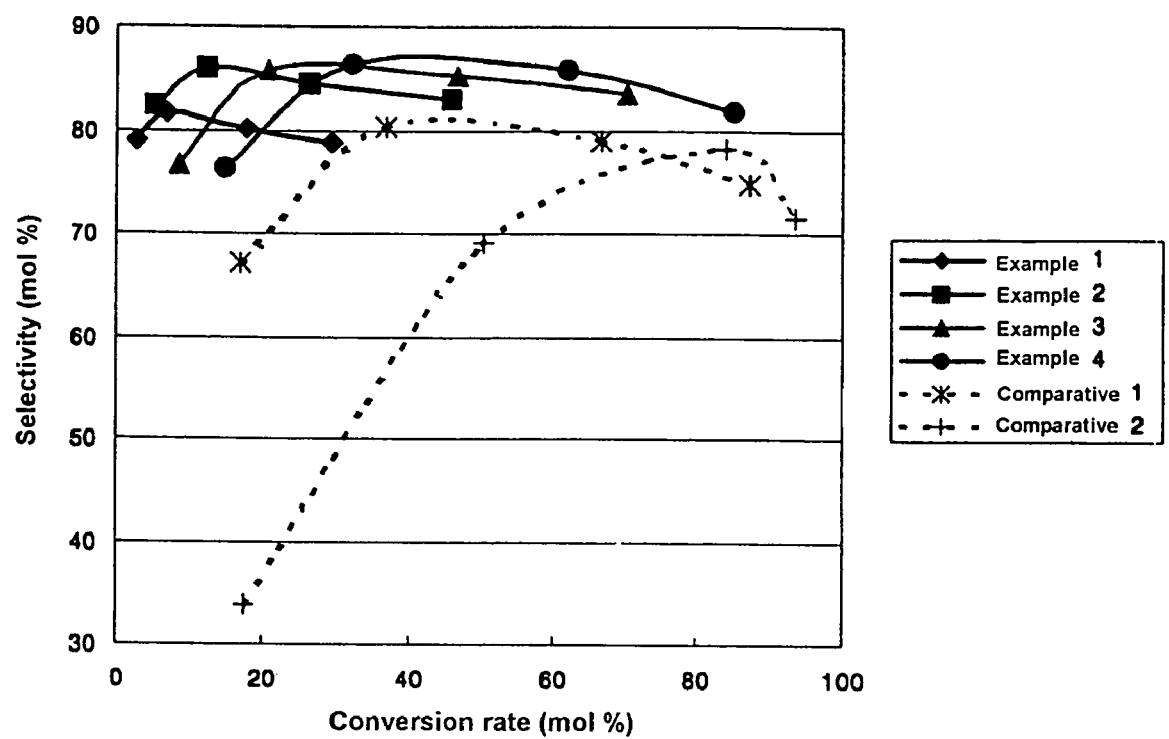

METHOD FOR PREPARING CATALYST FOR PARTIAL OXIDATION OF METHYLBENZENES

TECHNICAL FIELD

The present invention relates to a method for preparing a catalyst for partial oxidation of methylbenzenes. Specifically, the present invention relates to a novel method for preparing a catalyst which is suitable for producing corresponding aromatic aldehydes with high selectivity by gas phase oxidation of methylbenzenes with oxygen.

This application claims the benefit of Korean Patent Application No. 10-2005-41971 filed May 19, 2005 in Korea, which is hereby incorporated by reference in its entirety.

BACKGROUND ART

Aromatic aldehydes have aldehyde groups having high reactivity, and so have been widely used. Especially, terephthalaldehyde having two aldehyde groups at para position has been gained attention as raw material for medicinal products, agrochemicals, pigments, liquid crystal polymers, or plastic having heat resistance.

As conventional methods for the preparation of terephthalaldehyde, there are dehydration method of intermediate by chlorination of p-xylene, and hydrogenation method of dimethyl terephthalate. However, the above conventional methods are not suitable for economical mass production of terephthalaldehyde since the processes are complicated and are carried out under high pressure and environmental unfriendly condition.

In order to solve these problems, continuous efforts have been exerted into developing a mass production method of terephthalaldehyde by gas phase oxidation of p-xylene with molecular oxygen.

For example, Japanese Patent Publication No. 47-002086 discloses a complex oxide catalyst having the W and Mo ratio ranges of from 1:1 to 20:1. Japanese Patent Publication No. 48-047830 discloses a catalyst comprising V and Rb or Cs. U.S. Pat. No. 3,845,137 discloses a catalyst consisting of two components of W and Mo and one or more components selected from the group consisting of Ca, Ba, Ti, Zr, Hf, Tl, Nb, Zn, and Sn. Also, U.S. Pat. No. 4,017,547 discloses a catalyst consisting of Mo oxide, W oxide or silicotungstic acid and Bi oxide.

However, in case of using the catalysts of these inventions, the selectivity and yield of terephthalaldehyde were low, and so their industrial practicality has been limited.

Also, U.S. Pat. No. 5,324,702 discloses a catalyst distributing a first component selected from the group consisting of Fe, Zn, Zr, Nb, In, Sn, Sb, Ce and Bi, and a second component selected from the group consisting of V, Mo and W, on a deboronized borosilicate crystal molecular sieve by chemical vapor deposition (CVD). This catalyst showed relatively higher conversion rate of p-xylene and yield of terephthalaldehyde than conventional catalysts. However, in case of using the catalyst, there has been a limit to increase the selectivity due to various by-products, and so it has been difficult to separate and purify the by-products accordingly.

Also, U.S. Pat. No. 6,458,737 discloses a catalyst comprising a major component of W and one or more components selected from the group consisting of Sb, Fe, Co, Ni, Mn, Re, Cr, V, Nb, Ti, Zr, Zn, Cd, Y, La, Ce, B, Al, Tl, Sn, Mg, Ca, Sr, Ba, Li, Na, K, Rb and Cs. The catalyst can provide high yield of terephthalaldehyde almost enough to have industrial practicality. However, the catalyst also has limitation in separation and purification since the selectivity of terephthalaldehyde is not so high, compared with high conversion rate of p-xylene. Also, the catalyst has problems in heat stability and life span since it comprises Sb component which is sublimated and lost at high temperature.

In short, in case of using the conventional catalysts, the yield of terephthalaldehyde was low. Or, the separation and purification of terephthalaldehyde were difficult due to low selectivity even though they have high yield. Also, it was difficult to prepare catalysts having homogeneous composition and performance since they had to use complex oxide having multi-component. Further, the industrial practical use of the catalysts has been limited due to their short life span resulting from comprising components whose heat stability is low.

On the other hand, Korean Patent Application No. 10-2004-0089376 filed by the present inventors disclosed a single component catalyst comprising tungsten oxide and fire-resistant inorganic carrier as optional component. In case of using the catalyst, it is easy to prepare homogenous catalyst, and advantageous in that terephthalaldehyde can be prepared in high selectivity and yield, compared with conventional complex oxide having multi-component. However, a catalyst having higher selectivity for preparing terephthalaldehyde has been still required because the future research trend of partial oxidation reaction process field is focused on development of a catalyst which can reduce the green house gas which is major by-product, and can increase the selectivity of an object product, which will be a very important standard for commercialization of the catalyst process.

DISCLOSURE OF THE INVENTION

Considering the above problems, the object of the present invention is to provide a method for preparing a catalyst for partial oxidation of methylbenzenes, which is suitable for producing corresponding aromatic aldehydes from methylbenzenes with high selectivity over a wide range of conversion rate.

Below, the present invention will be described in detail.

The present invention relates to a novel method for preparing a catalyst of the formula (1),

wherein, W represents tungsten atom, O represents oxygen atom, and x represents a value determined by oxidative state of W, preferably a value of 2 to 3, for partial oxidation of methylbenzenes.

Specifically, the method comprises:

(a) a step of preparing a solution or slurry of the compounds containing tungsten;

(b) a step of supporting the solution or slurry obtained in the step (a) on inorganic carrier;

(c) a step of drying the supported product obtained in the step (b); and (d) a step of calcining the dried product obtained in the step (c), characterized in that the ratio of the pore volume of inorganic carrier and the volume of the solution or slurry in the step (b) is 1:0.9~1.1.

Here, the term "methylbenzene" means any compound having one or more methyl groups directly joined to the benzene ring. As representative examples of methylbenzene, methylbenzenes containing 8 to 10 carbon atoms such as p-xylene, o-xylene, m-xylene, pseudocumene, mesitylene, and durene are included, but not limited thereto.

The use of the catalyst according to the present invention is to oxidize methylbenzenes by gas-phase oxidation reaction with the molecular oxygen to give corresponding aromatic aldehydes. Specifically, the use includes production of terephthalaldehyde and p-tolualdehyde from p-xylene; phthalaldehyde and o-tolualdehyde from o-xylene; isophthalaldehyde and m-tolualdehyde from m-xylene; 2-methylterephthalaldehyde, 2,4-dimethylbenzaldehyde, 2,5-dimethylbenzaldehyde, and 3,4-dimethylbenzaldehyde from pseudocumene; 3,5-dimethylbenzaldehyde, 5-methylisophthalaldehyde and 1,3,5-triformylbenzene from mesitylene; and 2,5-dimethylterephthalaldehyde, 4,5-dimethylphthalaldehyde, 2,4,5-trimethylbenzaldehyde, 2,4,5-triformyltoluene and 1,2,4,5-tetraformylbenzene from durene, but not limited thereto. Particularly, the oxidation catalyst of the present invention is suitable for producing terephthalaldehyde from p-xylene.

BRIEF DESCRIPTION OF THE DRAWINGS

Drawing 1 is a graphical representation of the reaction results for examples 1-4 and comparative examples 1 and 2.

BEST MODE FOR CARRYING OUT THE INVENTION

Hereinafter, each step of the present invention will be described in more detail.

The step (a) of the present invention is to prepare a solution or slurry of the compounds containing tungsten.

There is no specific limitation to the compounds containing tungsten, and so oxides, carbides, chlorides, sulfides, silicides, organic acid salt, or heteropolyacid, preferably ammonium metatungstate, may be used in addition to ammonium tungstate.

The solvents used for preparing a solution or slurry of the compounds comprising tungsten are not limited, either. Water, or alcohols including methanol, ethanol, propanol, and diols may be used as the solvents. It is advantageous to use water in the environmental aspect. The water includes distilled water and de-mineralized water.

There is no specific limitation to the concentration of tungsten in the solution or slurry, but a high concentration of tungsten is preferable to shorten the catalyst preparation time since it can reduce the number of times for repetitive supporting. The preferable concentration is 0.5~3 mmol/g. When the concentration is lower than 0.5 mmol/g, the number of times for repetitive supporting may be increased, whereas the tungsten may not be insoluble when the concentration is more than 3 mmol/g. It is preferable to use saturated solution to reduce the number of times for repetitive supporting. Also, it is preferable to prepare a solution rather than a slurry for homogeneity of the catalyst.

The step (b) of the present invention is to support the above solution or slurry on inorganic carrier, in which the ratio of the pore volume of inorganic carrier and the volume of solution or slurry in the step (b) is 1:0.9~1.1, preferably, 1:0.95~1.05. It is most preferable to support the same volume of solution or slurry of the compounds comprising tungsten as the pore volume of carrier. When the ratio is beyond the above range, the desired yield or selectivity cannot be obtained Among the above inorganic carriers, it is preferable to use one or more fire-resistant inorganic carriers selected from the group consisting of α-alumina, silica, titania, zirconia, and silicon carbide.

Also, the step (b) is preferable to be carried out under reduced pressure or vacuum condition since the reduced pressure or vacuum of the container having carrier enables the active ingredient to be supported up to the inner surface of the catalyst.

The steps (c) and (d) of the present invention are to dry and calcine the prepared catalyst.

There is no special limitation to the method or atmosphere in drying and calcining the catalyst in the present invention. The examples of the method include vacuum dry, refrigeration dry, spray dry, microwave dry, rotary evaporation, air dry, etc., but not limited thereto. The atmosphere can be under any of the air, an oxygen-rich or oxygen-lean atmosphere, a reducing atmosphere, an inert gas atmosphere, or vacuum.

The temperature condition of the above steps (c) and (d) is also not particularly limited, but preferable that the dry temperature is 80~200° C., and the calcination temperature is 300~700° C. When the above dry temperature is below 80° C., the dry efficiency may be decreased. When the dry temperature is more than 200° C., it could be bad to the catalyst performance. When the calcination temperature is below 300° C., it is difficult to remove the reaction impurities. When the temperature is above 700° C., the morphology of the catalyst may be changed. Also, the time condition of the above steps (c) and (d) is not particularly limited, but each step of (c) and (d) is preferable to be carried out for sufficient time like more than 2 hours.

Further, according to the present method, it is preferable that the above supporting and drying steps [steps (b) and (c)] are repeatedly carried out two or more times. The repetition number of times of the supporting and drying steps is not particularly limited, but more repetition number of times is advantage since the repetition number leads to increase of the amount of supported material, which results in increase of the conversion rate. That is, since the concentration of the compounds comprising tungsten in aqueous solution or slurry is limited, it is preferable for the steps (b) and (c) to be repeated at least two times, and at least three times is more preferable. Specifically, it is preferable for the steps (b) and (c) to be repeated until 80% or more of the pore volume of inorganic carrier is supported as the compounds comprising tungsten. In this case, the repetition number of times of the above steps depends on the concentration of the compounds comprising tungsten in aqueous solution or slurry.

In case of repeating the supporting and drying steps, first, the amount of aqueous solution or slurry of the compounds comprising tungsten corresponding to a pre-calculated pore volume of the carrier is poured into the container including inorganic carrier to support the solution or slurry on the carrier. Then, the resulting supported carrier are dried on 80~200° C. for 2 or more hours. The remaining pore volume is calculated by measuring the weight of the resulting carrier. And, the amount of the aqueous solution or slurry corresponding to the calculated pore volume is supported again on the carrier in the same manner as the above. As the repetition number of times is increased, the amount of supported material is increased. After the final supporting step is carried out, the resulting carrier is dried and calcined to prepare the final catalyst.

The shape of the inorganic carrier or prepared catalyst according to the present invention is not particularly limited, and can be any of sphere, pellet, ring, honeycomb, etc., and further can be not only molded products but also oxide or hydroxide powders, gels, sols, and so on.

Hereinafter, the present invention will be more specifically illustrated by the following examples. However, the following examples should not be construed as limiting the scope of the present invention in any way.

The conversion rate, selectivity, and one-pass yield in the reaction are defined, considering by-products, as follows.

Conversion rate(mole %)=(the number of moles of the reacting starting compound/the number of moles of the fed starting compound)×100

Selectivity(mole %)=(the number of moles of each product compound/the number of moles of the reacting starting compound)×(the number of carbon atoms of each product compound/the number of carbon atoms of the fed starting compound)×100

One-pass yield(mole %)=(the number of moles of each product compound/the number of moles of the fed starting compound)×(the number of carbon atoms of each product compound/the number of carbon atoms of the fed starting compound)×100

Example 1

An aqueous solution of ammonium metatungstate (2 mmol/g) as raw material containing tungsten was prepared. The container including α-alumina carrier, SA5205 60 g (Norton Co., 5 mm of sphere, about 15 ml of pore volume) that was preheated on 120° C. was treated with vacuum, and the above aqueous solution (15 ml) was poured into the container under reduced pressure. The carrier was dried on 120° C. for 18 hours, and calcining treatment was carried out thereto under the air atmosphere at 650° C. for 2 hours to obtain the final catalyst. The weigh percent of WOx component was 14.3% of the total weight of the obtained catalyst, and thus the catalyst having the composition of 14.3 wt % WOx/SA5205 was obtained.

The above catalyst (60 g) was poured into the conventional continuous reactor, and the reaction was carried out under the following conditions:

Reaction pressure: normal pressure
The ratio of gas reactant (volume ratio):
p-xylene/oxygen/nitrogen=0.25/6.25/93.5 (oxygen/p-xylene=25)
Feeding rate of gas reactant: 1.2 L/min
Space velocity (GHSV): 1500 hr$^{-1}$
Reaction temperature: 450, 500, 550, and 580° C.

The following examples and comparative examples are carried out under the same condition as the above unless mentioned otherwise. However, the space velocity can be varied depending on the kind of carrier and the amount of supported material. The reaction results are shown in Table 1.

Example 2

The catalyst was prepared in the same manner as Example 1 except that the supporting and drying steps are repeated two times. At first, an aqueous solution (15 ml) of ammonium metatungstate was supported on the carrier, and the supported carrier was dried on 120° C. for 2 hours. After calculating the pore volume of the dried catalyst, 12 ml of aqueous solution of ammonium metatungstate corresponding to the above pore volume was second supported on the carrier in the same manner as the first supporting. The next steps are carried out in the same manner as Example 1 to obtain the catalyst having 24.3 wt % of WOx/SA5205 ratio. The reaction results are shown in Table 1 and Drawing 1.

Example 3

The catalyst was prepared in the same manner as Example 2 except that the supporting and drying steps are repeated three times. Each of 15 ml, 12 ml, and 9.6 ml of aqueous solutions of ammonium metatungstate was used in the first, second and third supporting steps to obtain the catalyst having 31.7 wt % of WOx/SA5205 ratio. The reaction results are shown in Table 1 and Drawing 1.

Example 4

The catalyst was prepared in the same manner as Example 2 except that the supporting and drying steps are repeated six times. Each of 15 ml, 12 ml, 9.6 ml, 7.7 ml, 6.1 ml, and 4.9 ml of aqueous solutions of ammonium metatungstate was used in the first, second, third, fourth, fifth, sixth supporting steps to obtain the catalyst having 37.1 wt % of WOx/SA5205 ratio. The reaction results are shown in Table 1 and Drawing 1.

Comparative Example 1

The catalyst was prepared in the same manner as Example 1 except using a diluted solution of an aqueous solution of ammonium metatungstate (54.0 g) with 60 ml of water. The weigh percent of WOx component was 24.7% of the total weight of the obtained catalyst, and thus the catalyst having 24.7 wt % of WOx/SA5205 ratio was obtained. The reaction results are shown in Table 1 and Drawing 1.

Comparative Example 2

The catalyst was prepared in the same manner as Comparative Example 1 except using an aqueous solution of ammonium metatungstate (90.0 g) to obtain the catalyst having 34.2 wt % of WOx/SA5205 ratio. The reaction results are shown in Table 1 and Drawing 1.

TABLE 1

| | Reaction Temp. (° C.) | Conversion Rate (mole %) | Selectivity (mole %) | | One-pass yield (mole %) | |
|---|---|---|---|---|---|---|
| | | | TPAL | PTAL | TPAL | PTAL |
| Ex. 1 | 450 | 2.7 | 78.9 | 0.0 | 2.1 | 0.0 |
| | 500 | 7.0 | 81.7 | 3.9 | 5.7 | 0.3 |
| | 550 | 17.9 | 80.1 | 3.1 | 14.3 | 0.6 |
| | 580 | 29.4 | 78.8 | 4.1 | 23.2 | 1.2 |
| Ex. 2 | 450 | 5.1 | 82.3 | 0.0 | 4.2 | 0.0 |
| | 500 | 12.4 | 86.0 | 3.0 | 10.6 | 0.4 |
| | 550 | 26.4 | 84.4 | 3.2 | 22.3 | 0.8 |
| | 580 | 46.0 | 82.9 | 3.5 | 38.2 | 1.6 |
| Ex. 3 | 450 | 8.6 | 76.6 | 2.2 | 6.6 | 0.2 |
| | 500 | 21.0 | 85.8 | 3.1 | 18.0 | 0.7 |
| | 550 | 46.8 | 85.3 | 3.2 | 39.9 | 1.5 |
| | 580 | 70.1 | 83.6 | 3.2 | 58.6 | 2.2 |
| Ex. 4 | 450 | 14.9 | 76.3 | 4.2 | 11.3 | 0.6 |
| | 500 | 32.1 | 86.3 | 3.7 | 27.7 | 1.2 |
| | 550 | 61.8 | 85.8 | 3.4 | 53.0 | 2.1 |
| | 580 | 85.1 | 81.8 | 2.9 | 69.6 | 2.5 |
| Comparative Ex. 1 | 450 | 16.9 | 67.2 | 4.3 | 11.4 | 0.7 |
| | 500 | 36.7 | 80.3 | 3.7 | 29.5 | 1.4 |
| | 550 | 66.6 | 79.0 | 3.4 | 52.6 | 2.3 |
| | 580 | 87.4 | 74.8 | 3.3 | 65.4 | 2.9 |
| Comparative Ex. 2 | 450 | 17.7 | 33.9 | 4.8 | 6.0 | 0.8 |
| | 500 | 50.4 | 69.0 | 3.9 | 34.8 | 2.0 |
| | 550 | 84.1 | 78.1 | 2.7 | 65.7 | 2.3 |
| | 580 | 93.8 | 71.5 | 2.8 | 67.1 | 2.6 |

TPAL: terephthalaldehyde,
PTAL: p-tolualdehyde

As shown in the above Table 1 and Drawing 1, Examples 1 to 4 according to the present invention show that the maximum selectivity of TPAL is 80% or more, which is superior to Comparative Examples 1 to 2 using the conventional impregnation method. Particularly, it is shown that as the amount of supported material is increased by the repetitive supporting steps the conversion rate is increased, but the maximum selectivity of TPAL is maintained at a high level of 85% or more. Also, it is shown that the selectivity of TPAL is uniform over a wide range of conversion rate. On the contrary, Comparative Example 1 prepared by the conventional impregnation method shows that the TPAL selectivity at the same level of conversion rate is lower by certain degree, compared with Example 4 showing the similarly trend of conversion rate. Also, Comparative Example 2 improving the conversion rate by increasing the amount of supported material shows that not only the maximum selectivity to TPAL is low, but also the change of selectivity of TPAL according to change of the conversion rate is very big. Therefore, it is shown that the catalyst prepared by the present invention is advantageous in preparing the TPAL with high selectivity by maintaining very high selectivity of TPAL over a wide range of conversion rate.

INDUSTRIAL APPLICABILITY

The tungsten oxides catalyst oxidation of methylbenzenes prepared according to the present invention can maintain uniform selectivity even if the conversion rate is increased from increase of the amount of supported material. Thus, the present invention can prepare corresponding aromatic aldehydes with high selectivity from methylbenzenes.

What is claimed is:

1. A method for preparing a catalyst of formula (1) and partially oxidizing methylbenzenes using the catalyst; the formula (1):

WOx wherein, W represents tungsten atom, O represents oxygen atom, and x represents a value determined by oxidative state of W, comprising:

(a) a step of preparing a solution or slurry of the compounds comprising tungsten;
(b) a step of supporting the solution or slurry obtained in the step (a) on an inorganic carrier to obtain a catalyst;
(c) a step of drying the catalyst obtained in the step (b);
(d) a step of calcining the dried catalyst obtained in the step (c); and
(e) a step of gas-phase oxidizing methylbenzenes in the presence of the catalyst obtained in the step (d),
wherein the ratio of the pore volume of the inorganic carrier and the volume of the solution or slurry in the step (b) is 1:0.9 to 1:1.1.

2. The method according to claim 1, wherein the solvent used for the solution or slurry in the step (a) is water.

3. The method according to claim 1, wherein the compounds comprising tungsten is ammonium metatungstate.

4. The method according to claim 1, wherein the inorganic carrier in the step (b) is one or more selected from the group consisting of α-alumina, silica, titania, zirconia and silicon carbide.

5. The method according to claim 1, wherein the step (b) is carried out under reduced pressure or vacuum condition.

6. The method according to claim 1, wherein the step (c) is carried out at a temperature of 80 to 200° C.

7. The method according to claim 1, wherein the step (d) is carried out at a temperature of 300 to 700° C.

8. The method according to claim 1, wherein the steps (b) and (c) are repeated at least two times.

9. The method according to claim 1, wherein the gas-phase oxidation of methylbenzenes is carried out at a normal pressure and a temperature of 450 to 580° C.

* * * * *